(12) United States Patent
Marquis et al.

(10) Patent No.: US 8,851,127 B2
(45) Date of Patent: Oct. 7, 2014

(54) METHODS AND SYSTEMS FOR PHARMACEUTICAL COMPOUNDING

(75) Inventors: Brian Marquis, Bradford, MA (US); Douglas Lang, St. Louis, MO (US)

(73) Assignee: Express Scripts, Inc., St. Louis, MO (US)

( * ) Notice: Subject to any disclaimer, the term of this patent is extended or adjusted under 35 U.S.C. 154(b) by 581 days.

(21) Appl. No.: 13/099,297

(22) Filed: May 2, 2011

(65) Prior Publication Data
US 2012/0282143 A1 Nov. 8, 2012

(51) Int. Cl.
- *B65B 3/04* (2006.01)
- *A61K 31/57* (2006.01)
- *G05D 11/13* (2006.01)
- *B65B 3/00* (2006.01)

(52) U.S. Cl.
CPC ............... *B65B 3/003* (2013.01); *A61K 31/57* (2013.01); *G05D 11/132* (2013.01)
USPC ............ 141/18; 141/83; 141/85; 141/94; 141/102; 141/244; 141/286; 604/407

(58) Field of Classification Search
USPC ........... 141/18, 83, 85, 102, 94–95, 244, 286; 604/407, 67
See application file for complete search history.

(56) References Cited

U.S. PATENT DOCUMENTS

| | | | |
|---|---|---|---|
| 4,625,494 A * | 12/1986 | Iwatschenko et al. | 53/432 |
| 4,754,786 A * | 7/1988 | Roberts | 141/1 |
| 4,789,014 A * | 12/1988 | DiGianfilippo et al. | 141/83 |
| 6,450,215 B1 * | 9/2002 | Willemstyn et al. | 141/10 |
| 2005/0209547 A1* | 9/2005 | Burbank et al. | 604/5.01 |
| 2008/0169044 A1* | 7/2008 | Osborne et al. | 141/1 |
| 2011/0094619 A1* | 4/2011 | Steel et al. | 141/27 |

* cited by examiner

*Primary Examiner* — Timothy L Maust
*Assistant Examiner* — Timothy P Kelly
(74) *Attorney, Agent, or Firm* — Bryan Cave LLP

(57) ABSTRACT

Methods and systems for pharmaceutical compounding are described. In one embodiment a system comprises a solution of a pharmaceutical in an injection vehicle, the solution being contained in a vessel. The system also includes one or more tubes, a filter, and one or more valves. The system presents a sterile environment for compounding the solution.

18 Claims, 6 Drawing Sheets

METHODS AND SYSTEMS FOR PHARMACEUTICAL COMPOUNDING

FIELD

This application relates generally to systems and methods for compounding pharmaceuticals and/or preparing compounded pharmaceuticals for delivery to a patient.

BACKGROUND

Customized medications may be created for patients by compounding pharmaceuticals. Compounding pharmaceuticals generally includes combining one or more active or therapeutic ingredients with one or more carrier substances or mediums. The compounding process may be done for medically necessary reasons, such as to change the form of the medication from a solid pill to a liquid, to avoid a non-essential ingredient that the patient is allergic to, or to obtain the exact dose needed. The compounding process may also be done for voluntary reasons, such as adding favorite flavors to a medication.

DETAILED DESCRIPTION

Figure 1:
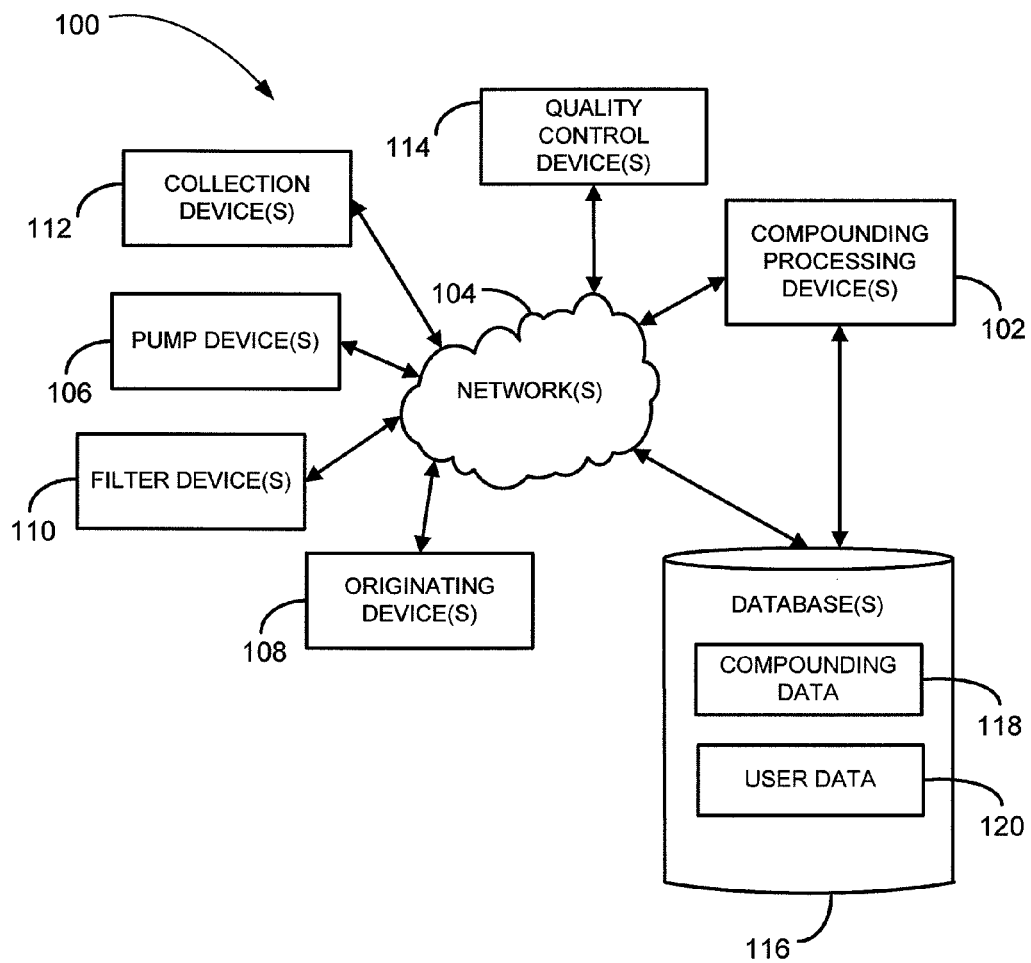
FIG. 1 is a block diagram of an example system, according to an example embodiment.

Methods and systems for pharmaceutical compounding are described. In the following description, for purposes of explanation, numerous specific details are set forth in order to provide a thorough understanding of example embodiments. It will be evident, however, to one of ordinary skill in the art that these embodiments may be practiced without these specific details.

One or more active ingredients and/or inactive ingredients may be combined with one or more delivery vehicles to create a compounded pharmaceutical. The compounded pharmaceutical may be provided for patient delivery via injection (e.g., as colloidal dispersions, emulsions, solutions, and/or suspensions), as irrigation for wounds or body cavities, as ophthalmic drops or ointments, in connection with tissue implants, as a suppository, as a topical treatment, as aqueous bronchial and/or nasal inhalations, as baths and soaks for live organs tissues, via ingestion, or otherwise.

In general a compounded pharmaceutical, and methods and systems of producing a compounded pharmaceutical, are suitable for use in connection with any active ingredient that requires and/or benefits from a high level of accuracy in weight of administered dose and/or level of purity. The compounded pharmaceutical may be sterile. In other example embodiments, the compounded pharmaceutical has a high level of purity, but may be less than sterile, e.g., the compounded pharmaceutical provided as a nutritional supplement for an immunocompromised patient.

An active ingredient may be any type of active ingredient that is compounded with a delivery vehicle (e.g., injection vehicle) for patient delivery. In one example, the active ingredient is progesterone. However other active ingredients, such as hormonal products, nutritional supplements, steroidal products, anti-microbial products, biologics, diagnostics, drugs, nutrients, and/or radiopharmaceuticals may be used.

An inactive ingredient may be, for example, one or more preservatives, solubalizing agents, pH balancing agents, agent for balancing isotonicity, and the like. Specific examples of inactive ingredients are benzyl alcohol and benzyl benzoate. An inactive ingredient for the compounded pharmaceutical may be selected based at least in part on the one or more active ingredient; for example, an inactive ingredient may be one that does not interfere with the active ingredient.

A delivery vehicle may be any appropriate vehicle to facilitate delivery of the active ingredient to a patient via an appropriate delivery method for the compounded pharmaceutical. In an example embodiment, sesame seed oil is a delivery vehicle for use in connection with a compounded pharmaceutical to be delivered via injection. In other embodiments, other delivery vehicles including peanut oil, olive oil, cottonseed oil, grapeseed oil, and/or ethyloleate, may be used. Other types of delivery vehicles may also be used.

The compounded pharmaceutical may be provided in connection with fertility treatments, and such compounded pharmaceutical may be customized for a particular patient.

By way of example, progesterone is a hormone that is prescribed to women for a variety of reasons. In the fertility context, progesterone may be used to promote a thicker lining of the uterine wall for implantation of the fertilized egg. Progesterone may also be used to, among other purposes, promote regular menstrual cycles and balance hormone levels to increase fertility and the chance of conception.

Because the hormone levels of women may vary, particularly the progesterone levels, compounding of progesterone may be used to vary and provide dosage levels that are customized for each patient. Compounding a customized dose of progesterone with a delivery vehicle, such as oil, may be used to create a dosage format that is easy to administer and absorb.

In one embodiment, progesterone may be provided in the form of a powder, micronized progesterone, hydroxyprogesterone, or the like to be used for a compounded pharmaceutical.

The methods and systems for pharmaceutical compounding may be used to provide a customized compounded pharmaceutical with a level of purity and in a dosage amount and/or form suitable for administration to a patient. For example, an injection vehicle may be selected based on a patient's allergies and/or sensitivities, a patient's preferences, a physician's preferences, and/or may otherwise be selected.

In an example embodiment, a pharmaceutical and an injection vehicle are provided for compounding. For example, a solution of oil and progesterone may be obtained by mixing together progesterone and oil.

Fertility treatments often require frequent administration of the prescribed compounded pharmaceutical. In an example embodiment, a single solution batch is compounded according to an example system and/or method of compounding pharmaceuticals and dispensed into collection vessels, each of which represents a dosage of a fertility treatment, such as a customized fertility treatment.

FIG. 1 is a block diagram of an example compounding system 100, according to an example embodiment. The compounding system 100 may include a compounding processing device 102 in communication with a pump device 106, an originating device 108, a filter device 110, a collection device 112, and/or a quality control device 114.

The compounding processing device 102 may receive information about a pharmaceutical to be compounded with a delivery vehicle (e.g., an injection vehicle) and/or an ingredient. A single pharmaceutical or multiple pharmaceuticals may be compounded with the delivery vehicle. The pharmaceutical(s) may be compounded with a single ingredient or multiple ingredients.

The compounding processing device 102 may control and/or monitor operations of one device or multiple devices of the compounding system 100. For example, the compounding processing device 102 may control and/or monitor operations of the pump device 106, the originating device 108, the filter device 110, the collection device 112, and the quality control device 114. In some embodiments, a portion of the control and/or monitoring functionality may be integrated within the devices 106-114.

The network 104 by which the devices 102, 106-114 communicate may include a Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Other conventional and/or later developed wired and wireless networks may also be used.

The pump device 106 in cooperation with an originating device 108 and/or a collection device 112 facilitates and/or controls the flow of a solution to be compounded through all or part of the compounding system 100. For example, the pump device 106 may provide a force to cause a compounded pharmaceutical and/or one or more of its component parts to flow or otherwise pass through one or more component parts of the compounding system 100.

The pump device 106 may receive solution information and/or other information from the compounding processing device 102. In some embodiments, the pump device 106 may control the amount and/or flow of solution out of an originating vessel, into one or more containment vessels, through a filter device, or otherwise. The pump device 106 may transmit information about the flow of solution out of the originating device 108, through the filter device 110, into the collection device 112, or otherwise. For example, the pump device 106 may transmit such information to the compounding processing device 102 and/or directly store the information in a database 116 as monitoring data. The pump device 106 may monitor pressure of a compounded pharmaceutical before and/or after passing through a filter device 110.

The originating device 108 receives the active ingredient or ingredients, any inactive ingredients, and delivery vehicle of a compounded pharmaceutical and facilitates or otherwise controls the flow of the compounded pharmaceutical through a system 100 and/or one or more of the components of a system (such as a filter device 110). Ingredients of a compounded pharmaceutical may be mixed at an originating device 108 or they may be pre-mixed. Ingredients of a compounded pharmaceutical may be measured at an originating device 108 or they may be pre-measured. Some ingredients may be pre-mixed and/or pre-measured and other ingredients may be mixed and/or measured at an originating device 108.

In some embodiments, the originating device 108 also includes a pressure source to create pressure to cause the compounded pharmaceutical to flow through the compounding system 100. In this embodiment, the pump device 106 may not be included in the compounding system 100.

In an example embodiment, the originating device 108 includes a mechanism and/or device to communicate to and/or otherwise provide information available to the compounding processing device 102 to indicate that the ingredients of the compounded pharmaceutical have been received at the originating device 108.

The filter device 110 filters a compounded pharmaceutical and/or one or more of its component parts as it flows or otherwise passes through all or part of the compounding system 100. The filter device 110 may monitor a compounded pharmaceutical and/or the pressure of the compounded pharmaceutical before, as, and/or after it passes through a filter. The filter device 110 may remove impurities from the compounded pharmaceutical. The filter device 110 may be targeted to a specific compounded pharmaceutical, type of compounded pharmaceutical, and/or targeted impurities. In an example embodiment, the filter device 110 is configured to remove undesired components of a compounded pharmaceutical while retaining the desired components and maintaining the efficacy of those desired components. In an example embodiment, the filter device 110 sterilizes a compounded pharmaceutical. In another example embodiment, the filter device 110 causes a compounded pharmaceutical to achieve a desired level of purity.

The filter device 110 may be monitored by the compounding processing device 102, either directly or indirectly. For example, the compounding processing device 102 may monitor the pressure and/or flow rate of a compounded pharmaceutical before it enters the filter device 110 and/or after it leaves the filter device 110. In one embodiment, the compounding processing device 102 verifies integrity of the filter device 110 by monitoring the pressure within the compounding processing system 100, which ordinarily should steadily increase over time. In one embodiment example, the compounding processing device 102 monitors the flow rate to determine whether it is decreasing over time. Any changes to the contrary may quickly indicate system failure of the compounding system 100.

The system pressure and/or the flow rate through the compounding system 100 may otherwise be monitored. In one example embodiment, system pressure and/or flow rate is monitored via human observation.

In another example embodiment, the system pressure and/or flow rate is monitored by the filter device 110. In such an embodiment, the filter device 110, in communication with the compounding processing device 102, may facilitate tests of the integrity of the filter device 110. For example, the filter device 110 may communicate information indicating whether or not the filter device 110 is intact, how fast solution is being pumped through the filter device 110, whether the filter device 110 is compromised, and the like.

Other tests of the integrity of the filter device 110 may be implemented by the quality control device 114, the compounding processing device 102, or may otherwise be implemented.

The collection device 112 receives a solution to be compounded and facilitates or otherwise controls the flow of the compounded pharmaceutical into one or more collection vessels of the collection device 112.

The collection device 112 may communicate the solution information, system information, and/or other feedback information to the compounding processing device 102. The collection device 112 may receive and/or provide information regarding the status of the compounding system 110, volumetric information, flow rate, pressure, temperature, viscosity and/or other information to and/or from the compounding processing device 102.

The collection device 112 may monitor, control, and/or otherwise facilitate dispensing of a compounded pharmaceutical into one or more collection vessels. For example, the collection device 112 may cause collection vessels to be filled sequentially, or to be otherwise filled. In an example embodiment, the collection device 112 may receive information from a weight diode coupled to a collection vessel about the volume of the collection container, the specific gravity of the solution, the overall expected weight of the collection container, the fill-rate of the container, and the like. The collection device 112 may provide such information to the compounding processing device 102.

The collection device 112 may include an automated vial filling subsystem. The automated vial filling subsystem may facilitate aseptic transfer, automatic control, computer monitoring, and the like.

In an example embodiment, the collection device 112 may include a pressure gauge that monitors solution information and/or system information. The collection device 112 may include a single pressure gauge or multiple pressure gauges.

The quality control device 114 receives and/or processes information about the integrity of the compounded pharmaceutical and/or one or more of its component parts; the functioning (e.g., proper functioning) of the pump device 106, the originating device 108, the filter device 110, and/or the collection device 112; and/or otherwise provides quality control functions. For example, the quality control device 114 may measure and/or monitor the weight, specific gravity, and/or viscosity of a compounded pharmaceutical at one or more points as it passes through the compounding system 100.

The quality control device 114 may communicate with the compounding processing device 102 to facilitate a test of the integrity and/or function of various components of the compounding system 100. A single test or multiple tests may be facilitated. For example, the quality control device 114 may communicate information indicating whether or not the filter device 110 is intact, how fast solution is being pumped through the filter device 110, whether the filter device 110 is compromised, and the like.

The compounding system 100 may include single devices 102, 106, 108, 110, 112, 114 or multiple devices of any one of the devices 102, 106, 108, 110, 112, 114 may be used. While the devices are shown discretely in FIG. 1, one or more of the devices 102, 106, 108, 110, 112, 114 may be integrated into a single device.

The compounding processing device 102 may be in communication with the database 116. The database 116 may store compounding data 118 and user data 120. The compounding data 118 may include information about the type of pharmaceutical, type of injection vehicle (or other delivery vehicle), the solution volume, the dosage amounts, the expected specific gravity of the solution, the desired temperature or temperature range of the solution, the expected viscosity of the solution, and the like. The compounding data 118 may also include batch data.

The user data 120 may include prescription information, patient information, physician information, and, the like.

In some embodiments, the database 116 may store data, e.g., the monitoring data, received from, provided to, and/or otherwise relating to the filter device 110, the pump device 106, the originating device 108, the collection device 112, and/or the quality control device 114. In some embodiments, the database 116 may store information relating to other hardware components of the compounding system 100 (such as tubing).

Figure 2:
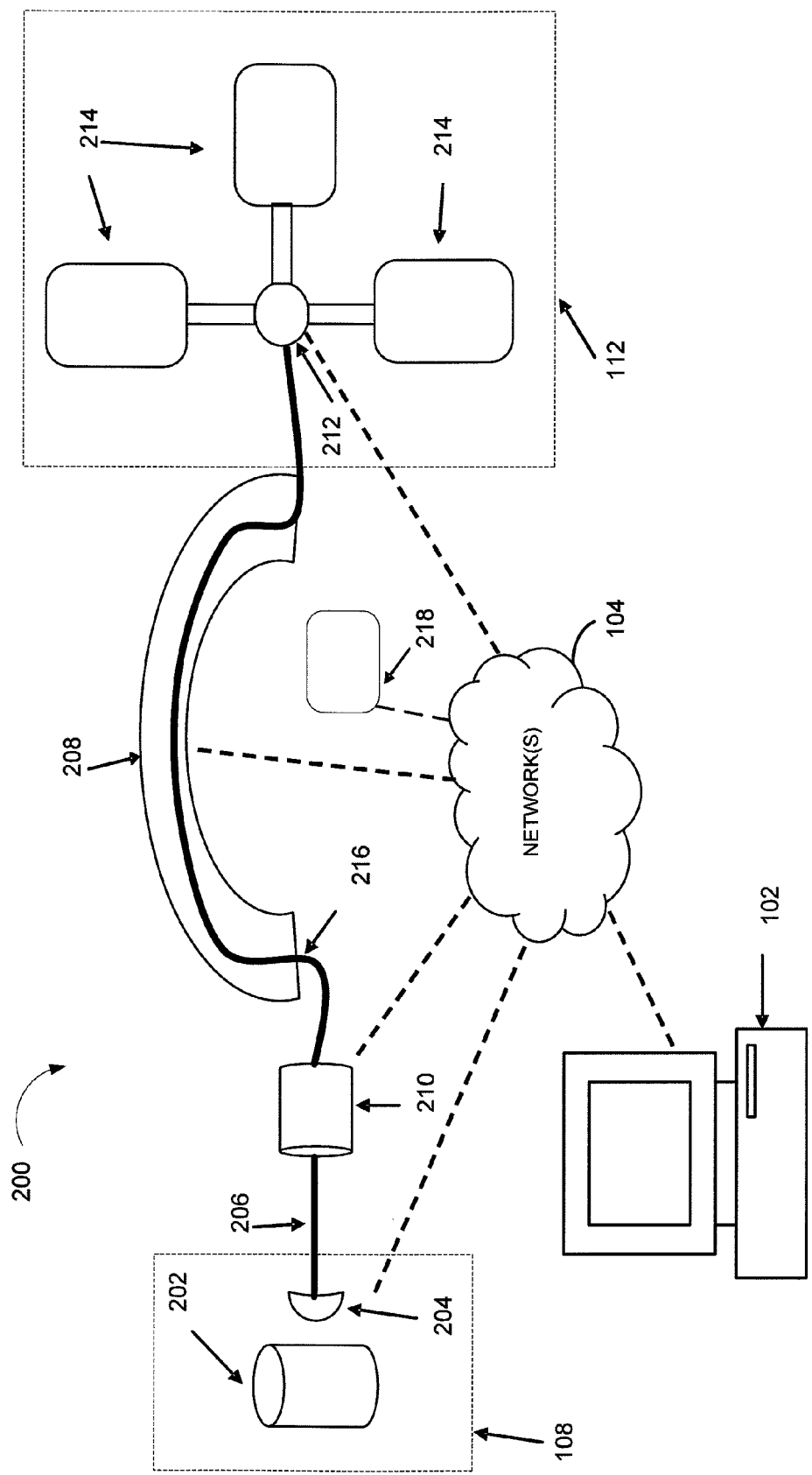
FIG. 2 illustrates an example system, according to an example embodiment.

FIG. 2 illustrates an example compounding system 200, according to an example embodiment. The compounding system 200 is an example configuration of the compounding system 100 (see FIG. 1). However, other configurations of the compounding system 100 may be used.

The originating device 108 is shown in FIG. 1 to include an originating vessel 202 and an originating valve 204. The originating vessel 202 receives a solution to be compounded by the compounding system 200. The solution may include one or more pharmaceuticals mixed with an injection vehicle. Other solution ingredients may be provided. The solution may be mixed to a desired consistency, either in the originating vessel 202 or before the solution is received into the originating vessel 202.

The originating device 108 may include an automated total parenteral nutrition ("tpn") device, e.g., that automatically dispenses patient-specific amounts of nutrients into the originating vessel 202 and/or a device adapted to automatically dispense other patient-specific amounts of an active ingredient, inactive ingredient, and/or delivery vehicle of a compounded pharmaceutical into an originating vessel 202 (or that is otherwise incorporated into the originating device 108).

A single originating vessel or multiple originating vessels may be used in the compounding system 200.

The originating vessel 202 may be a vessel that is compatible with the compounded pharmaceutical, e.g., that does not adversely react with and/or otherwise alter the efficacy of the compounded pharmaceutical or any of its ingredients. Examples of the originating vessel 202 include a beaker, bag, bottle, or a stainless steel container. Other types of suitable pharmaceutical containers may also be used. The originating vessel 202 may be contained in a laminar flow hood or other appropriate clean environment. The originating vessel 202 may be kept under ISO 5 or other appropriate environmental conditions to maintain a low particle count and minimize contamination. In an example embodiment, the originating vessel 202 is pre-sterilized and pyrogen-free.

The originating valve 204 may be a valve that is compatible with the compounded pharmaceutical, e.g., that does not adversely react with and/or otherwise alter the efficacy of the compounded pharmaceutical or any of its ingredients. The originating valve 204 may be a transfer tube connector valve. In one embodiment, the originating valve 204 is a one-way weighted valve. In an example embodiment, an originating value is a valve that is capable of being monitored (e.g., by the compounding processing device 102, the originating device 108, the quality control device 114, or otherwise) and controlled (e.g., turned on, turned off, and/or turned partially on by a compounding processing device 102, the originating device 108, or otherwise), and that does not require a breach in the connection site to perform such monitoring and/or controlling.

Other valves may be used. In an example embodiment, the originating valve 204 is formed as an integral part of the originating vessel 202.

In an example embodiment, the originating device 108 may include a nitrogen tank or other tank of inert air capable of being sealed with an originating vessel 202 to generate pressure within a system to cause a compounded pharmaceutical to move through the system. In an example embodiment, the originating device 108 may include one or more gauges or other devices to monitor the pressure and/or other characteristics of a compounded pharmaceutical in a originating vessel 202, at an originating valve, 204, and/or as it leaves an originating device 108.

A tube 206 may be coupled or otherwise connected to the originating vessel 202 and/or the originating valve 204. The tube 206 may be any type of sterile transfer tube or other transfer device or mechanism compatible with the solution. A tube may be made of a material that is compatible with the compounded pharmaceutical, e.g., that does not adversely react with and/or otherwise alter the efficacy of the compounded pharmaceutical or any of its ingredients. In an example embodiment, a tube includes walls that withstand an anticipated pressure range, e.g., pressures at which a compounded pharmaceutical may pass through the tube. In another example embodiment, a tube's internal diameter may affect the system pressure and may be selected accordingly.

The originating valve 204 may be placed in originating vessel 202 and/or may otherwise be configured to withdraw solution, or to permit or prevent withdrawal of solution, from the originating vessel 202 and into the tube 206. In an example embodiment, the tube 206, the originating vessel 202, and the originating valve 204 are provided as a single unit that has been pre-connected and pre-sterilized.

The pump device 106 may include a pumping mechanism 208. The pumping mechanism 208 may facilitate pulling the solution from the originating vessel 202 through at least a portion of the compounding system 200. In some embodiments, the pumping mechanism 208 is a peristaltic pump. In an example embodiment, the pumping mechanism 208 provides a steady amount of pressure such that a constant (or substantially constant) pressure is maintained at a filter 210 of a filter device 110. In another example, the pumping mechanism 208 introduces non-variable (or substantially non-variable) pressure into a system 200 to facilitate movement of a compounded pharmaceutical through the system. A pumping mechanism may produce an amount of pressure that is sufficient to allow a compounded pharmaceutical to pass through a filer 210 but not in excess of the pressure at which the filter 210 is likely to break or otherwise fail. Other types of pumps may also be used for the pumping mechanism.

In an example embodiment, the pump device 106 includes a mechanism to set a flow rate produced by the pumping mechanism 208. A flow rate may be set automatically (e.g., via the compounding processing device 102, the pump device 106, or otherwise) or manually.

Other systems, such as a system in which the originating device 108 includes one or more components to generate pressure within the system, do not include a pump device.

The filter device 110 may include a filter 210 to filter solution received from the originating vessel 202 and facilitate compounding of the solution. In an example embodiment, the filter 210 is a 0.22 micron sterile capsule filter, such as those available from Baxa. In other examples, the filter 210 may be a nucleopore filter, such as a nucleopore filter available from Millipore; the filter 210 may be a filter available from Pall or other filter providers. The filter 210 may be a disk filter, cartridge, etc. that may or may not contain a pre-filter. In an example embodiment that includes a pre-filter, the pre-filter is a 5 micron pre-filter. A filter may be hydrophilic or hydrophobic. A filter may be selected based on the characteristics of the compounded pharmaceutical and the impurities targeted for filtering. In other example embodiments the filter 210 may be an air filter. Other types of filters suitable for use in compounding processes may also be used.

The collection device 112 may include a collection valve 212 and a collection vessel 214. A single collection vessel or multiple collection vessels may be used.

The collection vessel 214 may be a vessel that is compatible with the compounded pharmaceutical, e.g., that does not adversely react with and/or otherwise alter the efficacy of the compounded pharmaceutical or any of its ingredients. Very generally, the collection vessel 214 may be a sterile container. Examples of sterile containers include sterile collection bags, vials or syringes. The collection vessel 214 may be selected based on the intended method of delivery of the compounded pharmaceutical to a patient. In some embodiments, the collection vessel 214 is adapted to hold a specific quantity, or a specific quantity range, of a compounded pharmaceutical, such as a quantity or quantity range identified by volume. The collection vessel 214 may hold in the range of about 100 to about 5000 milliliters. The collection vessel 214 may hold at least 100, 500, 1000, 1500, 2000, 2500, 3000, 3500, 4000, 4500, or 5000 milliliters. The collection vessel 214 may hold more than 5000 milliliters.

In an example embodiment, the collection vessel 214 is coupled to a weight diode. Information from the weight diode related to the volume of the collection container, the specific gravity of the solution, the overall expected weight of the collection container, the fill-rate of the container, and the like may be received by the compounding processing device 102, the collection device 112, and/or may otherwise be received.

Typically, the collection valve 212 is a transfer tube connector valve. In one example embodiment, the collection valve 212 is a stopcock valve. In one example embodiment, the collection valve 212 is a stopcock valve that is used to couple to a single collection vessel or multiple collection vessels of the same or varying size. For example, in one embodiment, the collection valve 212 is a three-way stopcock valve coupled to two 1000 milliliter collection vessels and a 2000 milliliter collection vessel. The collection valve 212 may be a valve that is compatible with the compounded pharmaceutical, e.g., that does not adversely react with and/or otherwise alter the efficacy of the compounded pharmaceutical or any of its ingredients. In an example embodiment, the collection value 212 is a valve that is capable of being monitored (e.g., by the compounding processing device 102, the collection device 112, the quality control device 114, or otherwise) and controlled (e.g., turned on, turned off, turned partially on, and/or switched by a compounding processing device 102, the collection device 108, or otherwise), and that does not require a breach in the connection site to perform such monitoring and/or controlling.

A flow rate of the pumping mechanism 208 (or other device used to introduce pressure into the compounding system 200) may be interrelated with and/or used to introduce a desired dosage amount of a compounded pharmaceutical into the collection vessel 214. Thus, at a flow rate setting of 50 milliliters per hour, the amount that is introduced into the collection vessel 214 could be measured based on the elapsed time during which the collection vessel is filled. However, the pump device 106 may have a mechanism to set a flow rate wherein the flow rate is based upon a pumped material with a specific gravity of 1 (e.g., water). A compounded pharmaceutical will have a specific gravity that is based upon the specific gravities of its ingredients, which specific gravity may be different than 1. Accordingly, a flow rate setting may be calculated (based on the difference between a specific gravity of 1 and the specific gravity of the compounded pharmaceutical) to achieve a desired actual flow rate (e.g., a desired actual flow rate of 50 milliliters per hour). A calculated actual flow rate may used in determining the amount of compounded pharmaceutical received by a collection vessel. Such a calculation may be made via the compounding processing device 102, the collection device 112, or may be otherwise made.

Tubes 206, 216 may be used to receive and transport a solution through the compounding system 200. The tubes 206, 216 may be appropriately coupled to the originating valve 204, the filter 210, the pumping mechanism 208, and/or the collection valve 212. For example, the tubes 206, 216 may be coupled to another system component with a pre-sterilized component, the tubes 206, 216 may be inserted into a system component (such as the originating valve 204, the filter 210, the pumping mechanism 208, and/or the collection valve 212) by gravity, friction, and the like.

The originating valve 204, the tube 206, the pumping mechanism 208, the filter 210, the collection valve 212, and/or the tube 216 may be configured with a feedback mechanism that communicates the solution information and/or system information. A single feedback mechanism or multiple feedback mechanisms may be used. The information may be received by the compounding processing device 102 or otherwise may be transmitted or received. For example, the originating valve 204, the tube 206, the pumping mechanism 208, the filter 210, the collection valve 212, and/or the tube 216 may be configured with an RFID transponder to communicate information regarding the status of the system, volumetric information, flow rate, pressure, temperature, viscosity and/or other information about the solution to the compounding processing device 102. In one embodiment, the originating valve 204, the tube 206, the pumping mechanism 208, the filter 210, the collection valve 212, and/or the tube 216 may include a pressure gauge that monitors solution information and/or system information and provides the information to the compounding processing device 102.

In one embodiment, the tubes 206, 216, the filter 210, the originating valve 204, the pumping mechanism 208, and the collection valve 212 are configured as a closed, sterile system. In another embodiment, at least a portion of the tubes 206, 216, the filter 210, the originating valve 204, the collection valve 212, and the pumping mechanism 208 may be configured as closed, sterile subsystems.

In general, the term sterile reflects that something is free from living germs or microorganisms, aseptic, and/or in compliance with U.S. Pharmacopeia's (USP) Revised General Chapter 797. In general, the term closed system refers to a system is sterilized and isolated from its surroundings by a boundary or that admits no transfer of contamination across it. When such a closed system consists of multiple subparts or subsystems, each such subpart or subsystem is sterile and is surrounded by a boundary that admits no transfer of contamination across it.

The quality control device 114 may include an imaging device 218. The imaging device 218 may be installed alongside the pump device 106, the originating device 108, the filter device 110, the collection device 112, and/or the tubes 206, 216 to monitor the solution and/or or the various hardware of the devices. A single imaging device or multiple imaging devices may be used. The imaging devices 218 may include, by way of example, infrared cameras, 3-D imaging cameras, video cameras and the like. The information may then be received by the compounding processing device 102. For example, infrared cameras may image the flow of the solution at various points along the compounding system 200. The cameras may communicate information about the flow rate of the solution to the compounding processing device 102. The compounding processing device 102 may use this information to adjust the speed of the pumping mechanism 208.

For example, the compounding processing device 102 may communicate with a camera coupled to and/or adjacent to the filter 210 in order to determine whether the filter 210 is intact, how fast the solution is being pumped through the filter 210, whether the filter 210 is compromised, and the like.

Figure 3:
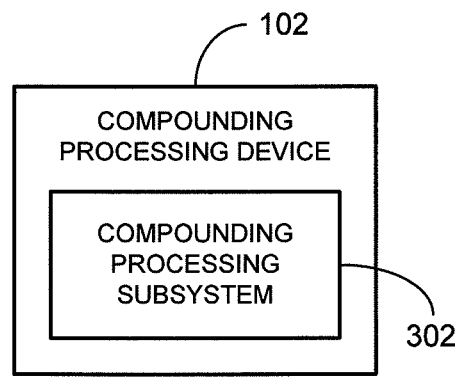
FIG. 3 illustrates an example compounding processing device that may be deployed in the system of FIG. 1, according to an example embodiment.

FIG. 3 illustrates a compounding processing device 102, according to an example embodiment. The compounding processing device 102 may be deployed in the compounding system 100, the compounding system 200, or may otherwise be deployed.

The compounding processing device 102 includes a compounding processing subsystem 302. The compounding processing subsystem 302 may receive information about a particular pharmaceutical or batch to be compounded (such as prescription order information included in the compounding data 118); control and/or monitor the rate/time, date/time, length of filtering time, pumping, volume, viscosity, temperature, pressure, users, and the like; compare the monitoring data from lot to lot for statistical analysis over time; identify and correct possible or suspected failures of the compounding system not easily detected by compounding personnel, such as loss of pressure indicating filter failure; and/or perform other functions.

The compounding processing subsystem 302 may monitor the pumping pressure, the flow rate of the solution through one or more tubes and/or the filter device 110, or other information related to the pumping of the solution by the pump device 106. The compounding processing subsystem 302 may receive information from the pump device 106, the originating device 108, the filter device 110, the collection device 112, the quality control device 114 and/or may otherwise receive information about compounding system 100 and/or one or more of its component parts.

The compounding processing subsystem 302 may control the operation of the pump device 106, the originating device 108, the filter device 110, the collection device 112, and/or the quality control device 114.

Figure 4:
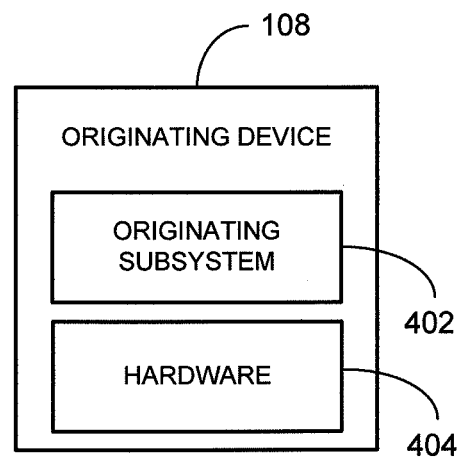
FIG. 4 illustrates an example originating device that may be deployed in the system of FIG. 1, according to an example embodiment.

FIG. 4 illustrates an originating device 108, according to an example embodiment. The originating device 108 may be deployed in the compounding system 100, the compounding system 200, or may otherwise be deployed.

The originating device 108 includes an originating subsystem 402. The originating subsystem 402 may communicate the solution information, system information, and/or other feedback information to the compounding processing device 102, or may otherwise provide such information. The originating subsystem 402 may receive and/or provide information regarding the status of the compounding system 100, volumetric information, flow rate, pressure, temperature, viscosity and/or other information to and/or from the compounding processing device 102.

Figure 5:
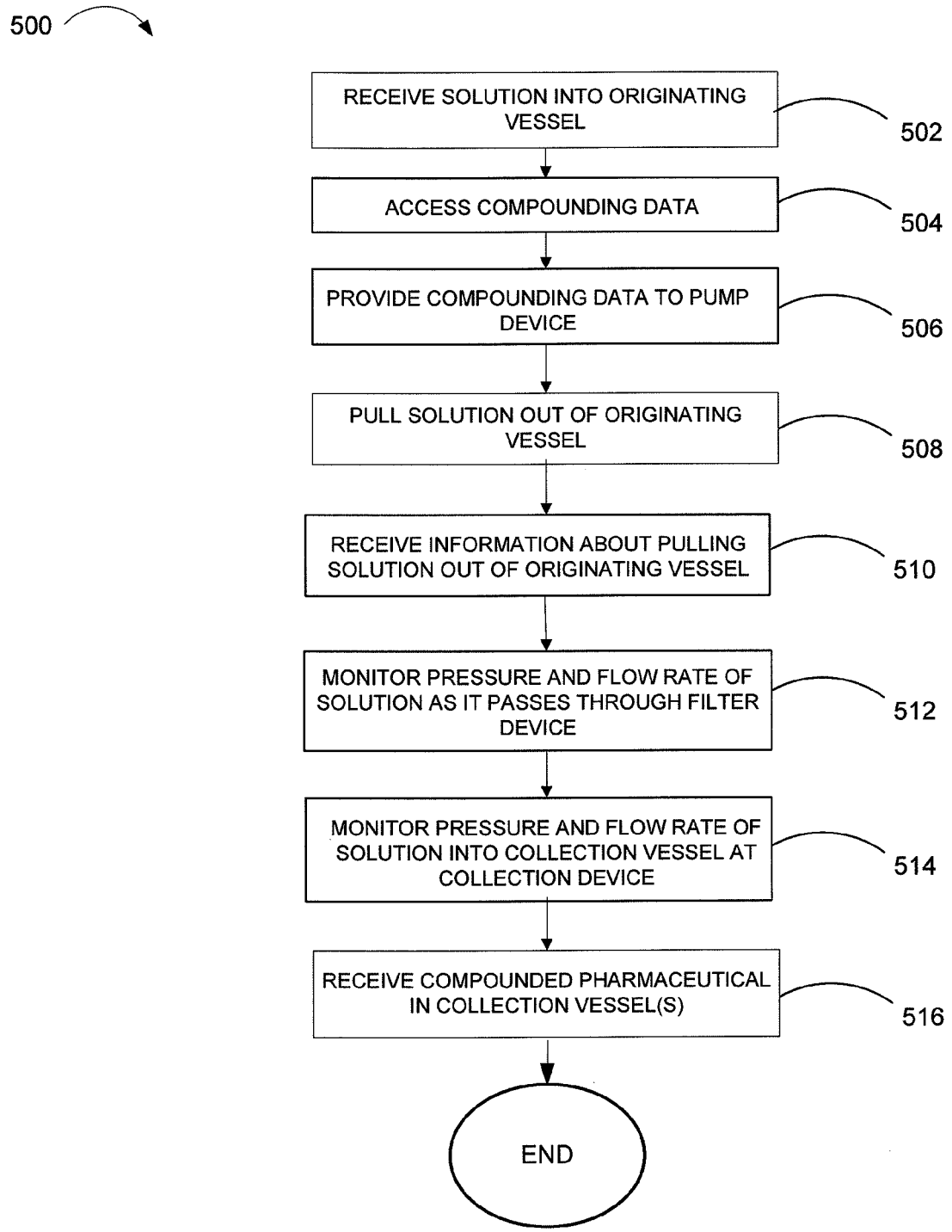
FIG. 5 is a block diagram of a flowchart illustrating an example system, according to an example embodiment.

FIG. 5 illustrates a method 500 for compounding a pharmaceutical according to an example embodiment. The method 500 may be performed by one or more of the devices 102, 106, 108, 110, 112, 114, or may be otherwise performed.

A solution to be compounded is received in the originating vessel 202 at block 502.

The compounding data 118 associated with the solution is accessed at block 504. The compounding data 118 may be accessed from the database 116, received through a user interface (e.g., by a worker manually entering this information), received from the originating device 108, or otherwise accessed.

Some or all of the compounding data 118 is provided to the pump device 106 at block 506. The compounding data 118 may be transmitted over the network 104 from the compounding processing device 102 or may otherwise be provided. For example, the compounding data 118 about the expected specific gravity, weight, and/or viscosity of the compounded pharmaceutical may be provided at block 506.

The pump device 106 may then use the compounding data 118 received from the compounding processing device 102 to pull the solution out of the originating vessel 108 at block 508. For example, and as discussed above, the specific gravity of the compounded pharmaceutical may be used to determine the flow rate at which the pump should be set. The compounding data 118 may represent information about the pressure range at which the filter will function properly without failing, which may be used to calculate the amount of pressure to be generated by the pump device 106.

At block 510, the compounding data 118, such as information about pulling solution out of an originating vessel may be provided to the compounding processing device 102. For example, the compounding data 118 that represents information about calculated the actual flow rate, desired dosage quantity, or otherwise may be used to determine when a collection value should be open to a particular collection vessel and/or when it should be closed. The monitoring data may be used in addition to or instead of the compounding data for such purposes.

The pumping pressure and the flow rate of the solution through the filter device 110 are monitored at block 512. The pressure and flow rate may be monitored by the compounding processing device 102, by the filter device 110, by the quality control device 114, by human observation, and/or may be otherwise monitored.

The pressure and flow rate of the solution at the collection device 112 is measured at block 514. The pressure and flow rate may be monitored by the compounding processing device 102, by the collection device 112, by the quality control device 114, by human observation, and/or may be otherwise monitored.

The compounded pharmaceutical is received into the collection vessel 214 of the collection device 112 at block 516. A filled collection vessel may be weighed, e.g., via a weight diode coupled to the collection vessel 214. Other information about a filled collection vessel and/or the compounded pharmaceutical may be measured and/or collected.

In some embodiments, after completion of the operations performed at block 516, a separate bubble point test may be performed to test the integrity of the filter 210.

Figure 6:
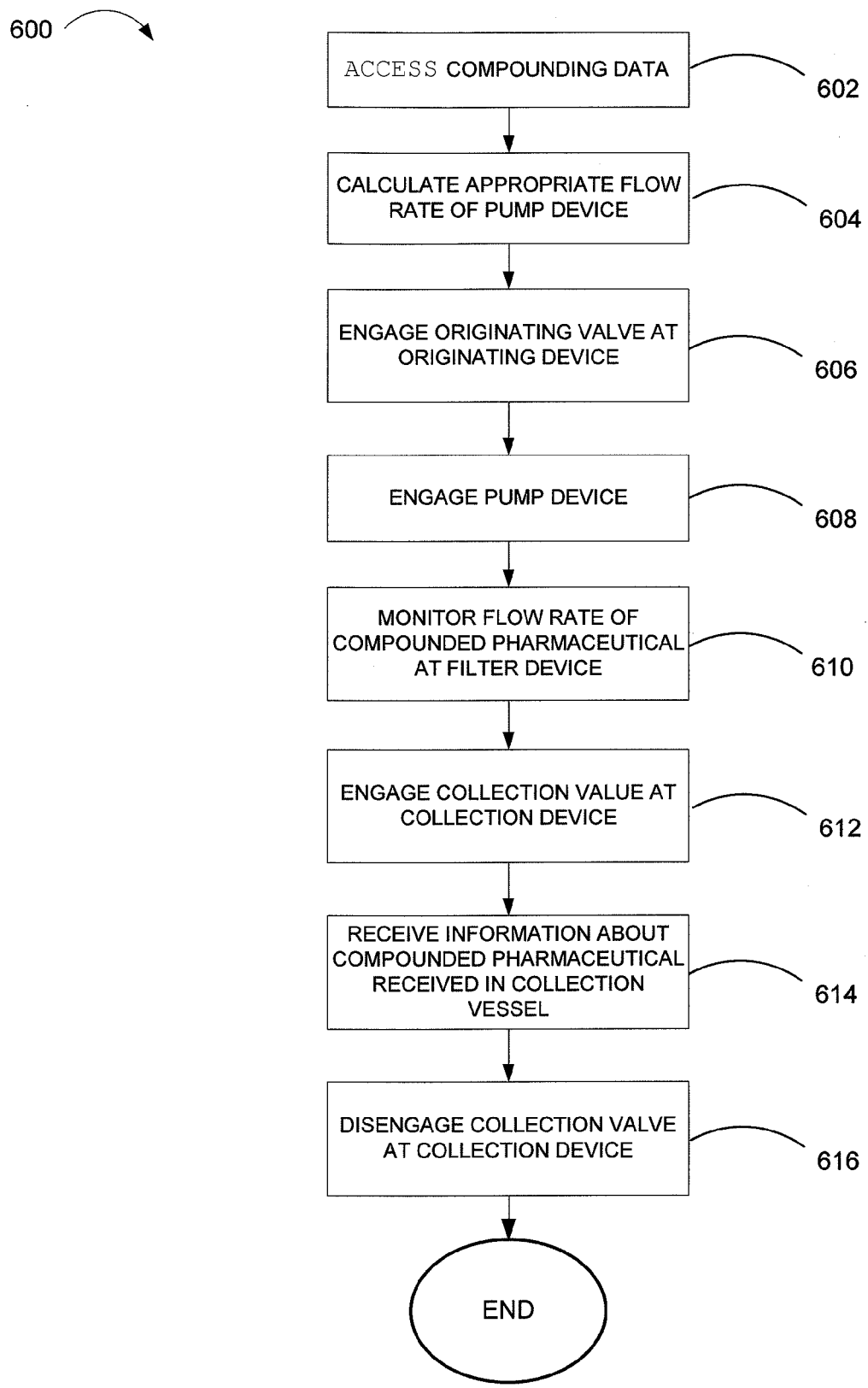
FIG. 6 is a block diagram of a flowchart illustrating an example method for facilitating compounding a pharmaceutical, according to an example embodiment.

FIG. 6 illustrates a method 600 for facilitating compounding a pharmaceutical according to an example embodiment. The method 600 may be performed by the compounding processing device 102 or may be otherwise performed.

The compounding data 118 is accessed at block 602. The compounding data 118 accessed at block 602 may be the compounding data providing information to calculate an appropriate flow rate, information about the amount (whether measured by weight, volume, or otherwise) of the compounded pharmaceutical, and/or other information.

At block 604, an appropriate flow rate for the pump device 106 is calculated. The calculation of the flow rate may be based on the compounding data 118 accessed at block 602. In an embodiment, the monitoring data may be received and used in calculating flow rate. The calculated flow rate may be an actual flow rate and/or a set flow rate, e.g., as discussed above, if flow rate settings are based on a solution with a specific gravity of 1, the actual flow rate of a particular solution (e.g., a compounded pharmaceutical) may be different than the set flow rate.

The originating valve 204 is engaged, e.g., turned on to permit the flow of a compounded pharmaceutical out of a collection vessel, at block 606, and at block 608, the pump device 106 is engaged.

Information about the flow rate of the compounded pharmaceutical as it enters, passes through, and/or leaves the filter of the filter device 110 is received at block 610. Such information may be used to monitor filter integrity, as discussed above.

At block 612, the collection valve 212 is engaged at the collection device 112 to allow a compounded pharmaceutical to flow into or otherwise be received by the collection vessel 214.

Information received at block 614 may be used to monitor amounts received into the collection vessel 214 and/or determine when the desired dosage amount has been dispensed into the collection vessel 214.

At block 616, the collection valve 212 is disengaged when, e.g., information received at block 614 indicates the collection vessel 214 has been filled with a desired dosage amount of a compounded pharmaceutical.

Figure 7:
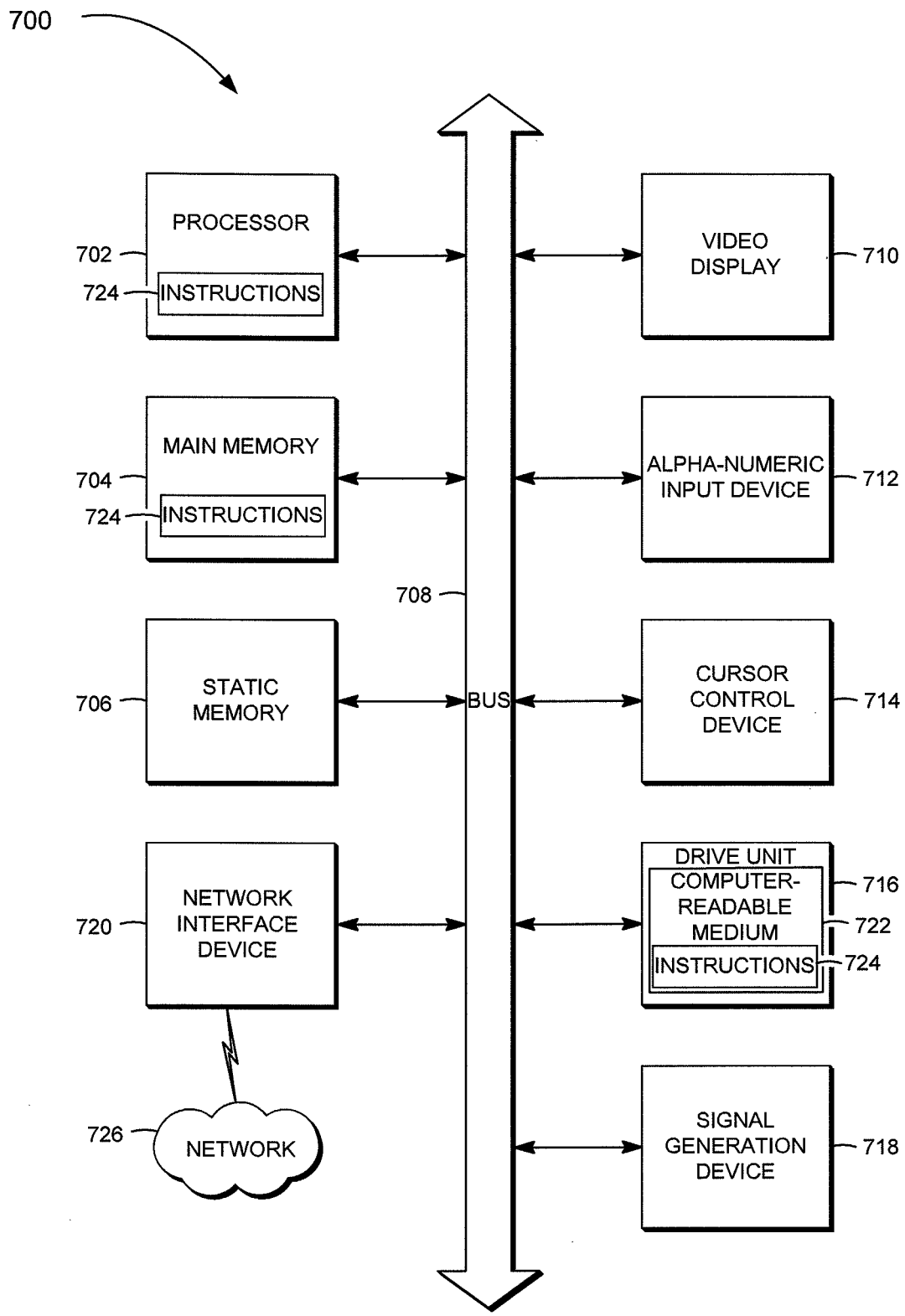
FIG. 7 is a block diagram of a machine in the example form of a computer system within which a set of instructions for causing the machine to perform any one or more of the methodologies discussed herein may be executed.

FIG. 7 shows a block diagram of a machine in the example form of a computer system 700 within which a set of instructions may be executed causing the machine to perform any one or more of the methods, processes, operations, or methodologies discussed herein. The compounding processing device 102, the pump device 106, the originating device 108, the filter device 110, the collection device 112, and/or the quality control device 114 may include the functionality of the one or more computer systems 700.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 700 includes a processor 702 (e.g., a central processing unit (CPU) a graphics processing unit (GPU) or both), a main memory 704 and a static memory 706, which communicate with each other via a bus 708. The computer system 700 may further include a video display unit 720 (e.g., a liquid crystal display (LCD) or a cathode ray tube (CRT)). The computer system 700 also includes an alphanumeric input device 712 (e.g., a keyboard), a cursor control device 714 (e.g., a mouse), a drive unit 716, a signal generation device 718 (e.g., a speaker) and a network interface device 720.

The drive unit 716 includes a computer-readable medium 722 on which is stored one or more sets of instructions (e.g., software 724) embodying any one or more of the methodologies or functions described herein. The software 724 may also reside, completely or at least partially, within the main memory 704 and/or within the processor 702 during execution thereof by the computer system 700, the main memory 704 and the processor 702 also constituting computer-readable media.

The software 724 may further be transmitted or received over a network 726 via the network interface device 720. While the computer-readable medium 722 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies. The term "computer-readable medium" shall accordingly be taken to include, but not be limited to, solid-state memories, and optical media, and magnetic media. In some embodiments, the computer-readable medium 722 is a non-transitory computer-readable medium.

Certain systems, devices apparatus, applications or processes are described herein as including a number of modules or component parts. A component part may be a unit of distinct functionality that may be presented in software, hardware, or combinations thereof. When the functionality of a component part is performed in any part through software, the component part includes a computer-readable medium. The component parts may be regarded as being communicatively coupled. The inventive subject matter may be represented in a variety of different embodiments of which there are many possible permutations.

In one embodiment, an originating device has an originating vessel and an originating valve. The originating device is configured to receive an active ingredient and a delivery vehicle to form a compound solution and control a flow of the solution. A filter device is connected to the originating device to receive and filter the solution. A pump device is operatively connected to the filter device and the originating device. The pump device is configured to facilitate a flow through the filter device. A collection device is coupled to the pump device and includes one or more collection vessels and a collection valve to receive the solution and control the flow into the one or more collection vessels. A processing device is communicatively connected to one or more of the originating device, the filter device, the pump device and the collection device to control operations thereof.

Thus, methods and systems for compounding pharmaceuticals have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A system comprising:
   a sterile subsystem, to compound a pharmaceutical, including an originating device, a filter device, a pump device, and a collection device;
   the originating device having an originating vessel and an originating valve, the originating device being configured to receive an active ingredient and a delivery vehicle to form a compound solution and control a flow of the solution;
   the filter device connected to the originating device to receive and filter the solution;
   the pump device operatively connected to the filter device and the originating device, the pump device being configured to facilitate a flow through the filter device;
   the collection device coupled to the pump device and including one or more collection vessels and a collection valve to receive the solution and control the flow into the one or more collection vessels;
   a processing device communicatively connected to one or more of the originating device, the filter device, the pump device and the collection device to control operations thereof; and
   an imaging device to monitor the flow of the solution adjacent the filter and to communicate information about flow rate of the solution to the processing device.

2. The system of claim 1, further comprising:
   a quality control device communicatively connected to the processing device and configured to monitor the solution.

3. The system of claim 1, wherein the processing device is adapted to monitor pump pressure, the flow rate, or both the pump pressure and the flow rate of the solution.

4. The system of claim 1, wherein the originating device is adapted to communicate solution information.

5. The system of claim 4, wherein the solution information includes one or more of volumetric data, flow rate, pressure, temperature and viscosity.

6. The system of claim 1, wherein the filter device monitors flow rate of the solution.

7. The system of claim 1, wherein the filter device includes a filter and the filter device verifies integrity of the filter by monitoring a change in pressure or a change in the flow rate.

8. The system of claim 7, wherein the filter includes a sterile filter.

9. The system of claim 1, wherein the collection vessel includes a sterile container.

10. The system of claim 1, further comprising:
    a weight diode coupled to the collection vessel and configured to transmit information to the processing device.

11. The system of claim 1, wherein the collection valve includes a stopcock valve.

12. The system of claim 11, wherein the stopcock valve is a three-way stopcock valve.

13. The system of claim 1, wherein the originating valve includes a one-way weighted valve.

14. The system of claim 1, wherein the originating vessel and the originating valve constitute an integral, unitary one-piece unit.

15. The system of claim 7, wherein the filter is adapted to remove undesired components of a compounded pharmaceutical while retaining desired components.

16. The system of claim 15, wherein the processing device monitors the pressure, the flow rate or both before and after the filter.

17. The system of claim 3, wherein the processing device monitors the pressure, the flow rate or both before and after the filter device.

18. A pharmaceutical preparing system comprising:
- an originating device having an originating vessel and an originating valve, the originating device being configured to receive an active ingredient and a delivery vehicle to form a pharmaceutical compound solution and control a flow of the solution, the originating device being adapted to automatically dispenses patient-specific amounts of the active ingredient from the originating vessel and adapted to automatically dispense patient-specific amounts of inactive ingredient, a delivery vehicle or combinations thereof, wherein the originating valve includes a one-way weighted valve;
- a filter device connected to the originating device to receive and filter the solution;
- a pump device operatively connected to the filter device and the originating device, the pump device being configured to facilitate a flow through the filter device at a flow rate associated with the compound solution;
- a collection device coupled to the pump device and including one or more collection vessels and a collection valve to receive the solution and control the flow into the one or more collection vessels, the collection device includes a weight diode configured to transmit weight information of the compound solution to the processing device;
- a processing device communicatively connected to one or more of the originating device, the filter device, the pump device and the collection device to control operations thereof, the processing device is adapted to monitor the pressure, the flow rate or both before and after the filter; and
- an imaging device to monitor the flow of the solution and to communicate information about the flow rate to the processing device;
- wherein the pump device is adapted to introduce a desired dosage amount of the compound solution to the collection vessel.

* * * * *